(12) United States Patent
Moon et al.

(10) Patent No.: US 12,313,611 B2
(45) Date of Patent: May 27, 2025

(54) GAS SENSOR AND MANUFACTURING METHOD THEREOF

(71) Applicant: ELECTRONICS AND TELECOMMUNICATIONS RESEARCH INSTITUTE, Daejeon (KR)

(72) Inventors: Seungeon Moon, Daejeon (KR); Jaewoo Lee, Daejeon (KR); Jong Jin Jung, Paju-si (KR); Jeong Hun Kim, Daejeon (KR); Do Joon Yoo, Paju-si (KR); Jong Pil Im, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 773 days.

(21) Appl. No.: 17/506,658

(22) Filed: Oct. 20, 2021

(65) Prior Publication Data

US 2022/0128498 A1    Apr. 28, 2022

(30) Foreign Application Priority Data

Oct. 22, 2020  (KR) .................. 10-2020-0137483
Jul. 1, 2021   (KR) .................. 10-2021-0086694

(51) Int. Cl.
  *G01N 25/30*   (2006.01)
  *B81C 1/00*    (2006.01)
  *G01N 33/00*   (2006.01)

(52) U.S. Cl.
  CPC ..... *G01N 33/0009* (2013.01); *B81C 1/00801* (2013.01); *B81B 2201/0214* (2013.01);
  (Continued)

(58) Field of Classification Search
  CPC ................ G01N 33/0009; G01N 25/30; B81C 1/00801; B81C 2201/0133;
  (Continued)

(56) References Cited

U.S. PATENT DOCUMENTS 7,861,575 B2 * 1/2011 Jun ................... G01N 33/0027
                                              73/25.05
8,683,847 B2 * 4/2014 Moon ................. G01N 27/128
                                              73/31.06
(Continued)

FOREIGN PATENT DOCUMENTS

JP    2005265758 A    9/2005
KR   20090061865 A    6/2009
(Continued)

*Primary Examiner* — Freddie Kirkland, III
(74) *Attorney, Agent, or Firm* — Rabin & Berdo, P.C.

(57) ABSTRACT

Provided is a gas sensor including a substrate, a first membrane disposed on the substrate, a heating structure disposed on the first membrane, a second membrane disposed on the heating structure, a sensing electrode disposed on the second membrane, and a sensing material structure disposed on the sensing electrode. Here, the substrate provides an isolation space defined by a recessed surface obtained as a portion of a top surface of the substrate is spaced downward from a bottom surface of the first membrane, and the first membrane provides a first membrane etching hole that vertically extends to connect a top surface and the bottom surface of the first membrane and is connected with the isolation space. Also, the first membrane etching hole has a diameter of about 3 μm to about 20 μm.

12 Claims, 7 Drawing Sheets

(52) U.S. Cl.
CPC ... *B81B 2203/0127* (2013.01); *B81B 2203/04* (2013.01); *B81C 2201/0133* (2013.01); *B81C 2201/0176* (2013.01); *B81C 2201/0178* (2013.01); *B81C 2201/0181* (2013.01)

(58) Field of Classification Search
CPC .... B81C 2201/0176; B81C 2201/0178; B81C 2201/0181; B81B 2201/0214; B81B 2203/0127; B81B 2203/04
See application file for complete search history.

(56) References Cited

U.S. PATENT DOCUMENTS

| | | | |
|---|---|---|---|
| 9,494,543 B2 | 11/2016 | Moon et al. | |
| 9,567,209 B1* | 2/2017 | Cheng | G01L 9/0044 |
| 10,017,379 B2 | 7/2018 | Rajaraman et al. | |
| 2004/0028602 A1* | 2/2004 | Franz | B01J 19/0093 |
| | | | 96/11 |
| 2004/0113802 A1* | 6/2004 | Green | G08B 21/16 |
| | | | 340/632 |
| 2005/0214740 A1 | 9/2005 | Ushio et al. | |
| 2006/0113198 A1* | 6/2006 | Sasaki | G01N 33/007 |
| | | | 204/426 |
| 2007/0089481 A1* | 4/2007 | Wansing | G01N 27/16 |
| | | | 73/23.2 |
| 2008/0128285 A1 | 6/2008 | Moon et al. | |
| 2010/0221148 A1 | 9/2010 | Oie et al. | |
| 2012/0198918 A1* | 8/2012 | Moon | G01N 27/128 |
| | | | 73/31.06 |
| 2013/0042669 A1* | 2/2013 | Humbert | G01N 27/128 |
| | | | 73/31.06 |
| 2013/0075255 A1 | 3/2013 | Moon et al. | |
| 2014/0208838 A1* | 7/2014 | Moon | G01N 27/16 |
| | | | 73/114.75 |
| 2016/0061761 A1* | 3/2016 | Shim | G01N 27/122 |
| | | | 436/151 |
| 2017/0129771 A1* | 5/2017 | Cheng | G01N 27/123 |

FOREIGN PATENT DOCUMENTS

| | | | | |
|---|---|---|---|---|
| KR | 1020120091981 A | 8/2012 | | |
| KR | 1020130034337 A | 4/2013 | | |
| KR | 1020140097714 A | 8/2014 | | |
| KR | 101498594 B1 | 3/2015 | | |
| KR | 20170114590 A * | 10/2017 | ......... | G01N 33/0009 |

* cited by examiner

GAS SENSOR AND MANUFACTURING METHOD THEREOF

CROSS-REFERENCE TO RELATED APPLICATIONS

This U.S. non-provisional patent application claims priority under 35 U.S.C. § 119 of Korean Patent Application Nos. 10-2020-0137483, filed on Oct. 22, 2020, and 10-2021-0086694, filed on Jul. 1, 2021, the entire contents of which are hereby incorporated by reference.

BACKGROUND

The present disclosure herein relates to a gas sensor and a manufacturing method thereof, and more particularly, to a gas sensor having low power consumption and structural stability and a manufacturing method thereof.

Researches on a gas sensor have been conducted for a long time. Currently, gas sensors having various types such as optical, electrochemical, semiconductor, catalytic combustion, and surface acoustic wave types are commercialized.

The optical type gas sensor or the electrochemical type gas sensor measures a conductivity caused by ion mobility or a spectrum variation of a gas to be measured. The semiconductor type gas sensor or the surface acoustic wave type gas sensor measures a conductivity variation caused by an oxidation/reduction reaction of a gas adsorbed to a sensing material or a surface wave propagation speed variation caused by the adsorbed gas. In general, the catalytic combustion type gas sensor determining whether a combustion gas exists or a concentration of the combustion gas by measuring temperature change caused by combustion heat generated through a reaction between the sensing material and the gas to be detected has been used as a methane such as LPG/LNG-based combustible sensing device.

A MEMS-type catalytic combustion type gas sensor having low electric power consumption and structural/mechanical/electrical stability even in case of a sudden impact is required in order to be mounted in mobile terminals or the internet of things and used in various services.

SUMMARY

The present disclosure provides a gas sensor capable of reducing electric power consumption and securing structural stability and a manufacturing method thereof.

The present disclosure also provides a gas sensor capable of preventing a damage of a membrane and a manufacturing method thereof.

The present disclosure also provides a gas sensor capable of improving a manufacturing yield and a manufacturing method thereof.

The object of the present invention is not limited to the aforesaid, but other objects not described herein will be clearly understood by those skilled in the art from descriptions below.

An embodiment of the inventive concept provides a gas sensor including: a substrate; a first membrane disposed on the substrate; a heating structure disposed on the first membrane; a second membrane disposed on the heating structure; a sensing electrode disposed on the second membrane; and a sensing material structure disposed on the sensing electrode. Here, the substrate provides an isolation space defined by a recessed surface obtained as a portion of a top surface of the substrate is spaced downward from a bottom surface of the first membrane, and the first membrane provides a first membrane etching hole that vertically extends to connect a top surface and the bottom surface of the first membrane and is connected with the isolation space. Also, the first membrane etching hole has a diameter of about 3 µm to about 20 µm.

In an embodiment, the heating structure may not overlap the first membrane etching hole in terms of a plane.

In an embodiment, the gas sensor may further include: a compensation electrode disposed on the second membrane; and a compensation material structure disposed on the compensation electrode.

In an embodiment, four first membrane etching holes may be provided.

In an embodiment, the first membrane etching hole may have a diameter of about 5 µm.

In an embodiment, the second membrane may provide a second membrane etching hole that vertically extends to connect a top surface and a bottom surface of the second membrane and is connected with the first membrane etching hole.

In an embodiment, the substrate may include a plurality of columns surrounded by the isolation space, and each of the plurality of columns may vertically extend to connect the bottom surface of the first membrane with the recessed surface.

In an embodiment, the substrate may include silicon (Si), aluminum oxide ($Al_2O_3$), magnesium oxide (MgO), quartz, gallium-nitrogen (GaN), gallium-arsenic (GaAs), polycarbonate (PC), polyethylene terephthalate (PET), polyethersulfone (PES), polyethylene naphthalate (PEN) or polyimide (PI), and each of the first membrane and the second membrane may include silicon oxide (SiOx) or silicon nitride (SiNx).

In an embodiment of the inventive concept, a method for manufacturing a gas sensor includes: laminating a first membrane on a substrate; forming a heating structure on the first membrane; laminating a second membrane on the first membrane and the heating structure; forming a second membrane etching hole by patterning the second membrane; forming a sensing electrode on the second membrane; forming a first membrane etching hole in the first membrane through the second membrane etching hole; and etching a portion of the substrate through the first membrane etching hole and the second membrane etching hole. Here, the forming of a portion of the substrate includes forming an isolation space by allowing a portion of a top surface of the substrate to be recessed downward, and the first membrane etching hole has a diameter of about 3 µm to about 20 µm.

In an embodiment, the heating structure may not overlap the first membrane etching hole in terms of a plane.

In an embodiment, the etching of a portion of the substrate may include allowing a plurality of columns surrounded by the isolation space to be remained, and each of the plurality of columns may vertically extend to connect a bottom surface of the first membrane with a recessed surface.

In an embodiment, each of the laminating of the first membrane on the substrate and the laminating of the second membrane on the first membrane and the heating structure may be performed by using thermal oxidation deposition, sputtering deposition, or chemical vapor deposition.

In an embodiment, four first membrane etching holes may be provided.

Particularities of other embodiments are included in the detailed description and drawings.

BRIEF DESCRIPTION OF THE FIGURES

The accompanying drawings are included to provide a further understanding of the inventive concept, and are incorporated in and constitute a part of this specification. The drawings illustrate embodiments of the inventive concept and, together with the description, serve to explain principles of the inventive concept. In the drawings.

DETAILED DESCRIPTION

Figure 1:
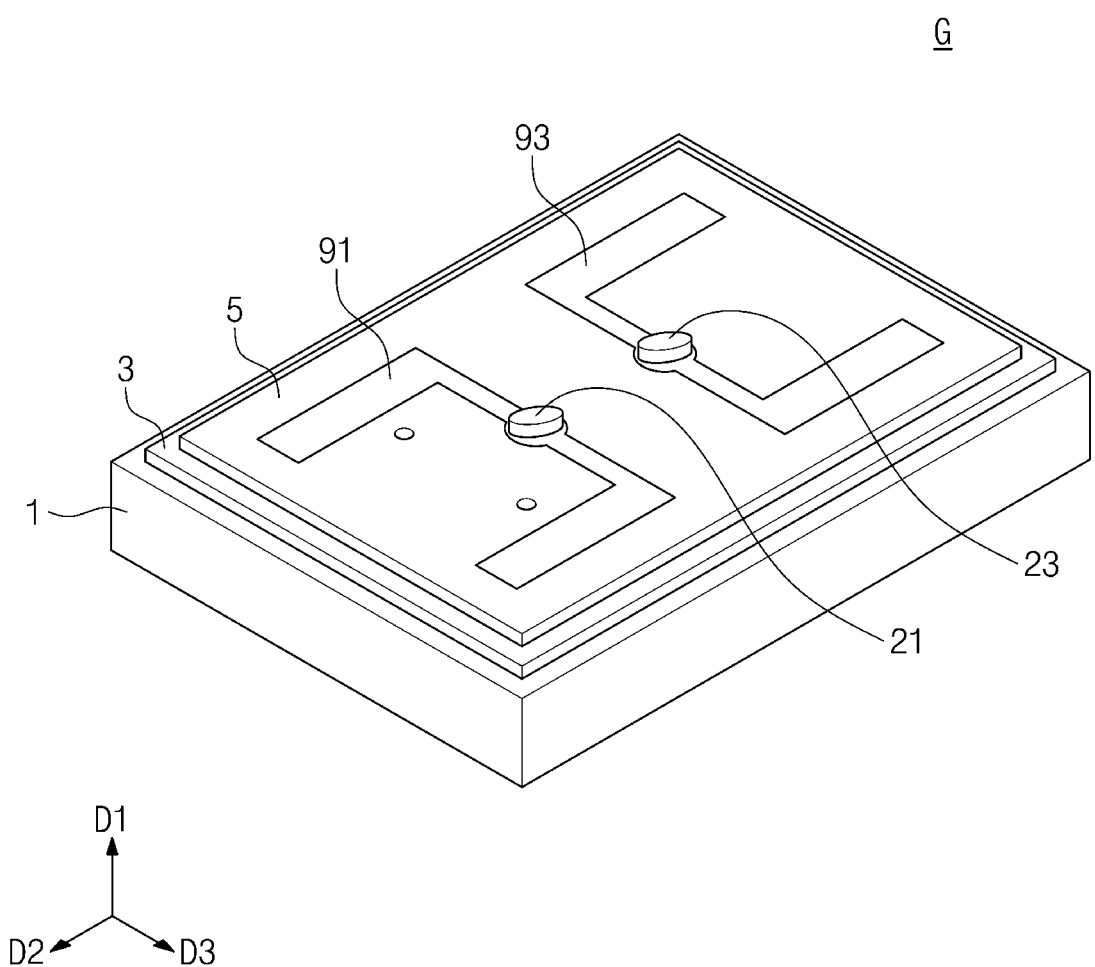
FIG. 1 is a perspective view illustrating a gas sensor according to an embodiment of the inventive concept.

Exemplary embodiments of the present invention will be described with reference to the accompanying drawings so as to sufficiently understand constitutions and effects of the present invention. The technical ideas of the inventive concept may, however, be embodied in different forms and should not be construed as limited to the embodiments set forth herein. Rather, these embodiments are provided so that this disclosure will be thorough and complete, and will fully convey the scope of the present invention to those skilled in the art. Further, the present invention is only defined by scopes of claims.

Like reference numerals refer to like elements throughout. The embodiment in the detailed description will be described with cross-sectional views and/or plan views as ideal exemplary views of the inventive concept. Also, in the figures, the dimensions of layers and regions are exaggerated for clarity of illustration. Areas exemplified in the drawings have general properties, and are used to illustrate a specific shape of a semiconductor package region. Thus, this should not be construed as limited to the scope of the present invention. Also, although various terms are used to describe various components in various embodiments of the inventive concept, the component are not limited to these terms. These terms are only used to distinguish one component from another component. Embodiments described and exemplified herein include complementary embodiments thereof.

In the specification, the technical terms are used only for explaining a specific exemplary embodiment while not limiting the present invention. In the specification, the terms of a singular form may include plural forms unless referred to the contrary. The meaning of "include," "comprise," "including," or "comprising," specifies a property, a region, a fixed number, a step, a process, an element and/or a component but does not exclude other properties, regions, fixed numbers, steps, processes, elements and/or components.

Hereinafter, the present invention will be described in detail by explaining preferred embodiments of the invention with reference to the attached drawings.

Figure 2:
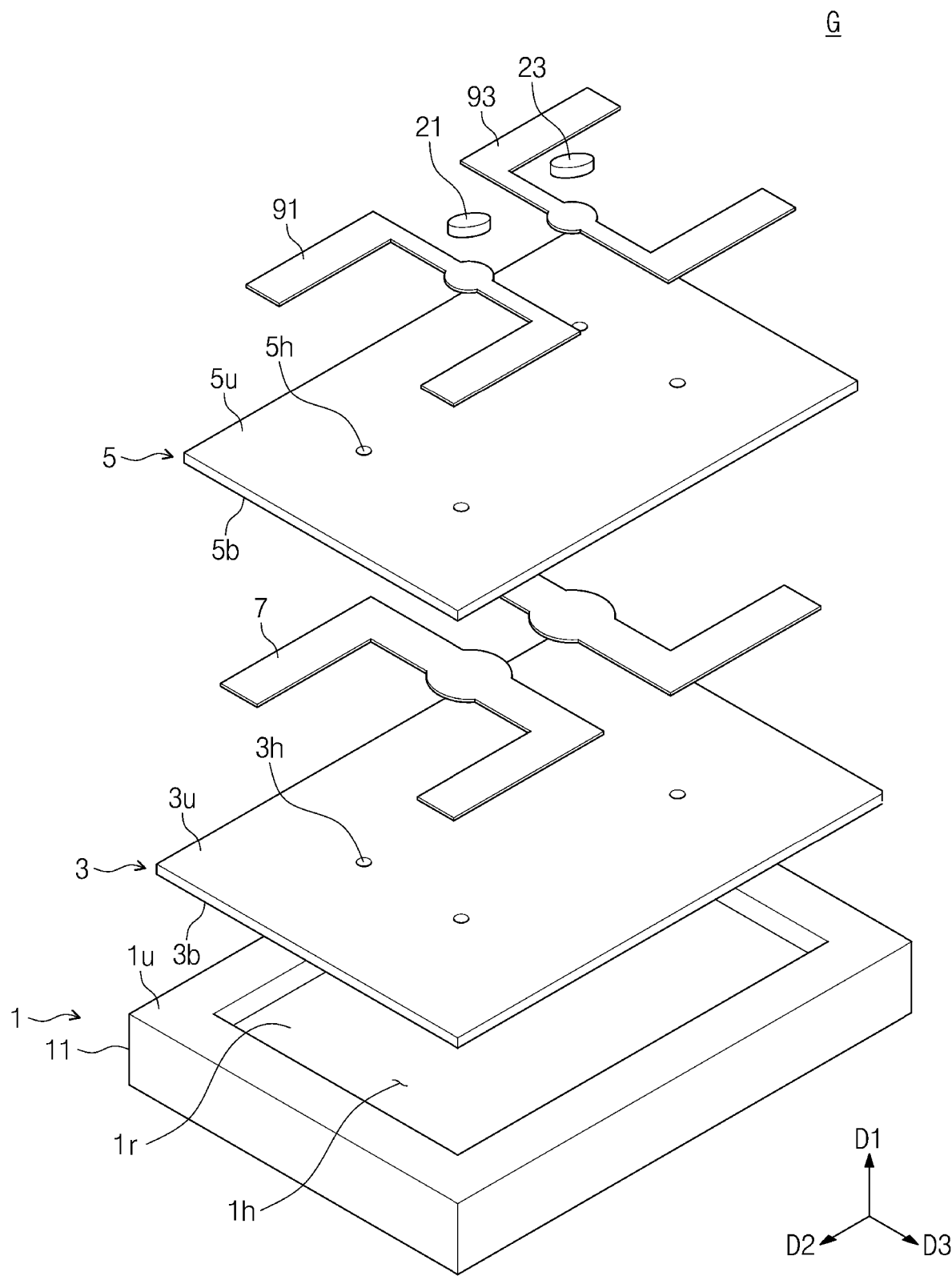
FIG. 2 is an exploded perspective view illustrating the gas sensor according to an embodiment of the inventive concept.

FIG. 1 is a perspective view illustrating a gas sensor according to an embodiment of the inventive concept, and FIG. 2 is an exploded perspective view illustrating the gas sensor according to an embodiment of the inventive concept.

Hereinafter, in FIG. 1, D1 may be referred to as a first direction, D2 crossing the first direction D1 may be referred to as a second direction, and D3 crossing the first direction D1 and the second direction D2 may be referred to as a third direction.

Referring to FIG. 1, a gas sensor G may be provided. The gas sensor G may be a catalytic combustion type gas sensor. That is, the gas sensor G may measure temperature change caused by combustion heat generated through a reaction between a gas and a sensing material. The gas sensor G may determine whether a combustible gas exists and/or a concentration of a combustible gas by detecting the temperature change. The gas sensor G may be a micro-electro mechanical systems (MEMS) based catalytic combustion type gas sensor. Referring to FIGS. 1 and 2, the gas sensor G may include a substrate 1, a first membrane 3, a heating structure 7, a second membrane 5, a sensing electrode 91, a sensing material structure 21, and a compensation material structure 23.

The substrate 1 may support the first membrane 3 or the like. Although the substrate 1 may include a silicon (Si) substrate, the embodiment of the inventive concept is not limited thereto. That is, the substrate 1 may include silicon (Si), aluminum oxide ($Al_2O_3$), magnesium oxide (MgO), quartz, gallium-nitrogen (GaN), gallium-arsenic (GaAs), polycarbonate (PC), polyethylene terephthalate (PET), polyethersulfone (PES), polyethylene naphthalate (PEN) or polyimide (PI). The substrate 1 may provide an isolation space 1h. That is, as a portion of a top surface 1u of a substrate body 11 is recessed downward, the isolation space 1h may be defined. A surface recessed downward by a predetermined length from the top surface 1u may be referred to as a recessed surface 1r. Thus, the isolation space 1h may be defined by the recessed surface 1r. Although the recessed surface 1r may be provided as a central portion of the top surface 1u of the substrate body 11 is recessed, the embodiment of the inventive concept is not limited thereto.

The first membrane 3 may be disposed on the substrate 1. The first membrane 3 may include silicon oxide (SiOx) and/or silicon nitride (SiNx). For example, the first membrane 3 may have a structure having a plurality of layers of the silicon oxide (SiOx) and/or the silicon nitride (SiNx). The first membrane 3 may have a thickness of about 0.2 μm to about 0.7 μm. More specifically, the first membrane 3 may have a thickness of about 0.3 μm. The first membrane 3 may be provided through a deposition process. For example, the first membrane 3 may be provided on the substrate 1 by a method such as thermal oxidation deposition, sputtering deposition, and/or chemical vapor deposition (CVD). The method will be described in detail with reference to FIG. 4. The first membrane 3 may provide a first membrane etching hole 3h. The first membrane etching hole 3h may vertically extend to connect a top surface 3u and a bottom surface 3b of the first membrane 3. The first membrane etching hole 3h may have a diameter of about 3 μm to about 20 μm. More specifically, the first membrane etching hole 3h may have a diameter of about 5 μm. The above-described diameter of the first membrane etching hole 3h may prevent the first membrane 3 from being damaged when a portion of the substrate 1 is etched through the first membrane etching hole 3h of the first membrane 3. That is, when the first membrane etching hole 3h has a diameter of about 3 μm to about 20 μm, the substrate 1 through the first membrane etching hole 3h may be smoothly etched while the first membrane 3 is not damaged. The first membrane etching hole 3h may be provided in plurality. For example, four first membrane etching holes 3h may be provided. However, the embodiment of the inventive concept is not limited thereto. A detailed description on the first membrane etching hole 3h will be described later.

The heating structure 7 may be disposed on the first membrane 3. In embodiments, the heating structure 7 may be disposed around a central portion of the top surface 3u of the first membrane 3. The heating structure 7 may not overlap the first membrane etching hole 3h on a plane. That is, in terms of the plane, the heating structure 7 may be horizontally spaced apart from the first membrane etching hole 3h. Thus, an additional hole may be unnecessary to be defined in the heating structure 7 for etching the substrate 1. However, the embodiment of the inventive concept is not limited thereto. For example, an etching hole may be defined in the heating structure 7. A detailed description regarding this will be described later. The heating structure 7 may be connected with an external circuit (not shown) by a bonding wire (not shown). The heating structure 7 may receive electric power to emit heat. That is, the heating structure 7 may increase a surrounding temperature thereof. The heating structure 7 may include metal such as gold (Au), tungsten (W), platinum (Pt) and palladium (Pd). However, the embodiment of the inventive concept is not limited thereto. For example, the heating structure 7 may include silicon or conductive metal oxide. The heating structure 7 may have a thickness of about 0.2 μm. However, the embodiment of the inventive concept is not limited thereto. As illustrated in FIG. 2, two heating structures 7 may be provided. However, hereinafter, the singular heating structure 7 will be described unless otherwise noted for convenience.

In embodiments, a bonding layer (not shown) may be further provided between the first membrane 3 and the heating structure 7. The bonding layer may bond the first membrane 3 and the heating structure 7. To this end, the bonding layer may include chrome (Cr) and/or titanium (Ti).

The second membrane 5 may be disposed on the first membrane 3 and the heating structure 7. The second membrane 5 may include silicon oxide (SiOx) and/or silicon nitride (SiNx). For example, the second membrane 5 may have a structure having a plurality of layers of the silicon oxide (SiOx) and/or the silicon nitride (SiNx). The second membrane 5 may insulate the heating structure 7 from the sensing electrode 91 and a compensation electrode 93. Also, the second membrane 5 may support the sensing electrode 91 and the compensation electrode 93. The second membrane 5 may have a thickness of about 0.2 μm to about 0.7 μm. More specifically, the second membrane 5 may have a thickness of about 0.3 μm. The second membrane 5 may be provided through a deposition process. The second membrane 5 may provide a second membrane etching hole 5h. The second membrane etching hole 5h may vertically extend to connect a top surface 5u and a bottom surface 5b of the second membrane 5. The second membrane etching hole 5h may overlap the first membrane etching hole 3h in terms of the plane. That is, the second membrane etching hole 5h may be disposed on the first membrane etching hole 3h. The second membrane etching hole 5h may have a diameter of about 3 μm to about 20 μm. More specifically, the second membrane etching hole 5h may have a diameter of about 5 μm. The above-described diameter of the second membrane etching hole 5h may prevent the second membrane 5 from being damaged when a portion of the substrate 2 is etched through the second membrane etching hole 5h of the second membrane 5. The second membrane etching hole 5h may be provided in plurality. For example, when four first membrane etching holes 3h are provided, four second membrane etching holes 5h may be also provided. However, the embodiment of the present invention is not limited thereto. A detailed description on the second membrane etching hole 5h will be described later.

The sensing electrode 91 may be disposed on the second membrane 5. The sensing electrode 91 may not overlap the second membrane etching hole 5h on the plane. That is, in terms of the plane, the sensing electrode 91 may be horizontally spaced apart from the second membrane etching hole 5h. Thus, an additional hole may be unnecessary to be defined in the sensing electrode 91 for etching the substrate 1. However, the embodiment of the inventive concept is not limited thereto. For example, an etching hole may be defined in the sensing electrode 91. A detailed description regarding this will be described later. The sensing electrode 91 may be connected to the sensing material structure 21. The sensing electrode 91 may electrically connect the sensing material structure 21 to the outside. The sensing electrode 91 may send a resistance value of the sensing material structure 21 to the outside. That is, when the resistance value of the sensing material structure 21 is changed, an external control unit (not shown) may recognize the changed resistance value through the sensing electrode 91. The sensing electrode 91 may include metal such as platinum (Pt), aluminum (Al), and/or gold (Au). However, the embodiment of the inventive concept is not limited thereto. For example, the sensing electrode 91 may include different metal such as conductive metal oxide. The sensing electrode 91 may be provided on the second membrane 5 through a deposition process. More specifically, the sensing electrode 91 may be provided by a method such as sputtering deposition, e-beam deposition, and/or chemical vapor deposition (CVD). Although not shown, the sensing electrode 91 may be connected to the control unit through a separate bonding wire.

The sensing material structure 21 may be disposed on the sensing electrode 91. The sensing material structure 21 may adsorb a gas. More specifically, when a gas is adsorbed to the sensing material structure 21, combustion heat may be generated. Thus, when a gas is adsorbed to the sensing material structure 21, a temperature of the sensing material structure 21 may be changed. When the temperature of the sensing material structure 21 is changed, a resistance value of the sensing material structure 21 may be changed. To this end, the sensing material structure 21 may include a material such as a carbon nano tube (CNT) and/or graphene. More specifically, the sensing material structure 21 may be provided by adding novel metal such as platinum and/or palladium to the carbon nano tube and/or graphene. The sensing material structure 21 may be provided through sol-gel, electrospinning, inkjet printing, screen printing, sputtering deposition, and/or chemical vapor deposition.

The compensation electrode 93 may be disposed on the second membrane 5. The compensation electrode 93 may not overlap the second membrane etching hole 5h on the plane. That is, in terms of the plane, the compensation electrode 93 may be horizontally spaced apart from the second membrane etching hole 5h. Thus, an additional hole may be unnecessary to be defined in the compensation electrode 93 for etching the substrate 1. However, the embodiment of the inventive concept is not limited thereto. For example, an etching hole may be defined in the compensation electrode 93. A detailed description regarding this will be described later. The compensation electrode 93 may be connected to the compensation material structure 23. The compensation electrode 93 may electrically connect the compensation material structure 23 to the outside. The compensation electrode 93 may send a resistance value of the compensation material structure 23 to the outside. That is, when the resistance value of the compensation material structure 23 is changed, an external control unit (not shown) may recognize the changed resistance value through the compensation electrode 93. The compensation electrode 93 may include metal such as platinum (Pt), aluminum (Al), and/or gold (Au). However, the embodiment of the inventive concept is not limited thereto. For example, the compensation electrode 93 may include different metal such as conductive metal oxide. The compensation electrode 93 may be provided on the second membrane 5 through a deposition process. More specifically, the compensation electrode 93 may be provided by a method such as sputtering deposition, e-beam deposition, and/or chemical vapor deposition (CVD). Although not shown, the compensation electrode 93 may be connected to the control unit through a separate bonding wire.

The compensation material structure 23 may be disposed on the compensation electrode 93. The compensation material structure 23 may adsorb a gas. More specifically, when a gas is adsorbed to the compensation material structure 23, combustion heat may be generated. Thus, when a gas is adsorbed to the compensation material structure 23, a temperature of the compensation material structure 23 may be changed. When the temperature of the compensation material structure 23 is changed, a resistance value of the compensation material structure 23 may be changed. To this end, the compensation material structure 23 may include a material such as a carbon nano tube (CNT) and/or graphene. The compensation material structure 23 may be provided through sol-gel, electrospinning, inkjet printing, screen printing, sputtering deposition, and/or chemical vapor deposition.

In embodiments, a protection layer may be disposed on the sensing electrode 91 and/or the compensation electrode 93. The protection layer may be made of a non-conductive material. The protection layer may be disposed only on a portion in which the sensing material structure 21 and the compensation material structure 23 are not disposed. The protection layer may include a silicon layer and/or a silicon nitride layer.

Figure 3:
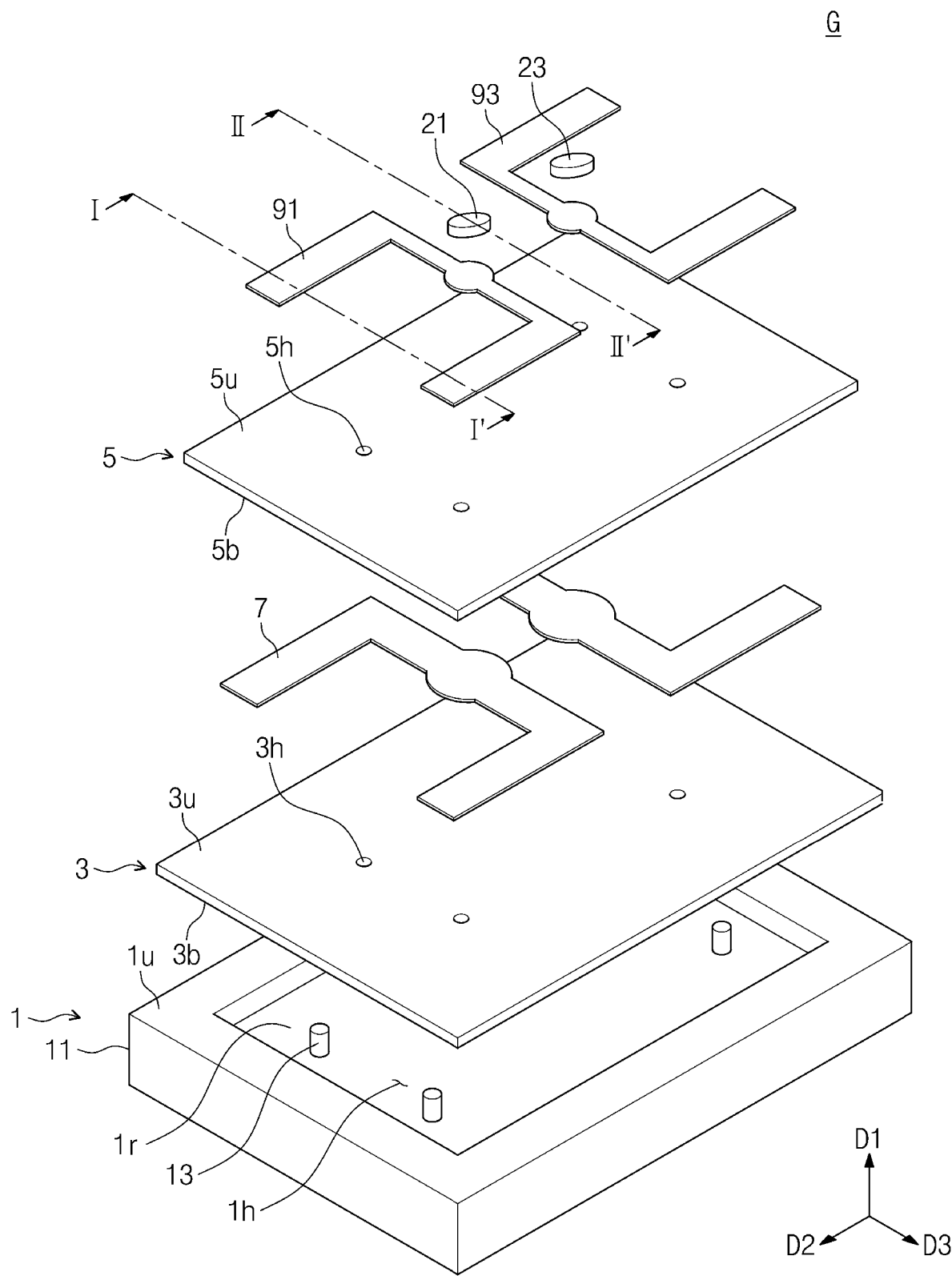
FIG. 3 is an exploded perspective view illustrating a gas sensor according to an embodiment of the inventive concept.

FIG. 3 is an exploded perspective view illustrating a gas sensor according to an embodiment of the inventive concept.

Hereinafter, features that are substantially the same as or similar to those described with reference to FIGS. 1 to 2 will be omitted for convenience.

Referring to FIG. 3, a substrate 1 may further include a column 13. The column 13 may be surrounded by an isolation space 1h. The column 13 may be connected to a recessed surface 1r. More specifically, the column 13 may extend upward by a predetermined length from the recessed surface 1r and be connected to a bottom surface 3b of a first membrane 3. The column 13 may support the first membrane 3 or the like. In embodiments, the column 13 may be provided in plurality. The plurality of columns 13 may be horizontally spaced apart from each other.

Figure 8:
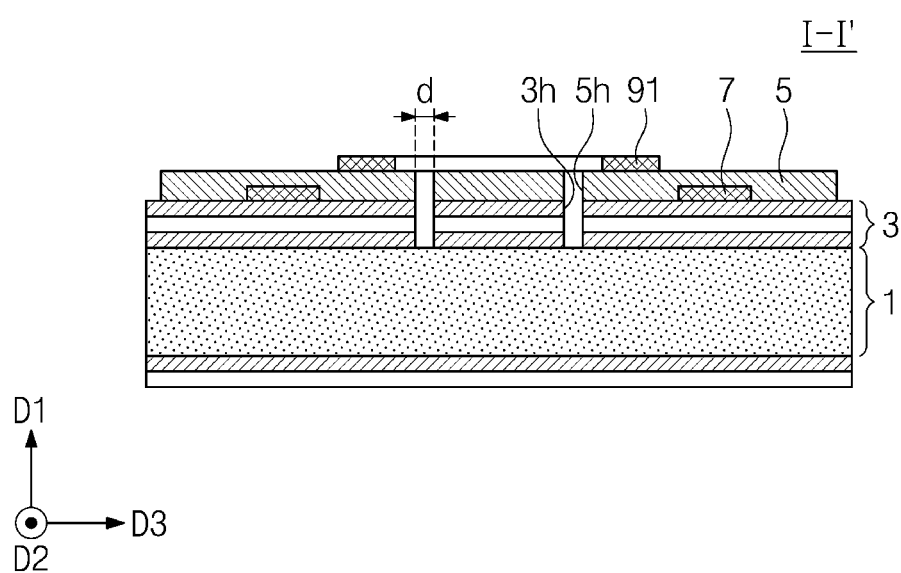
Figure 9:
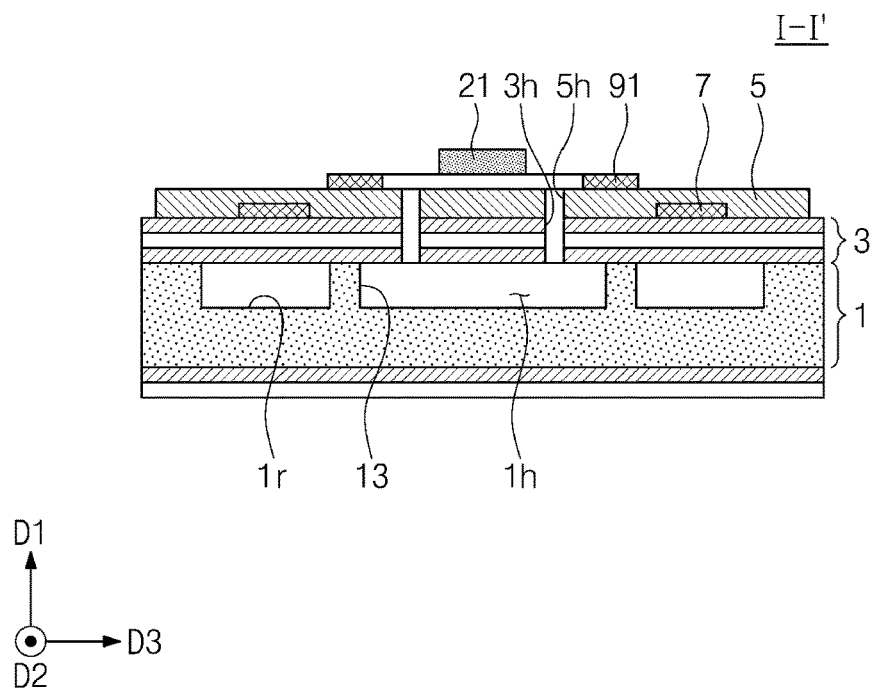
Figure 10:
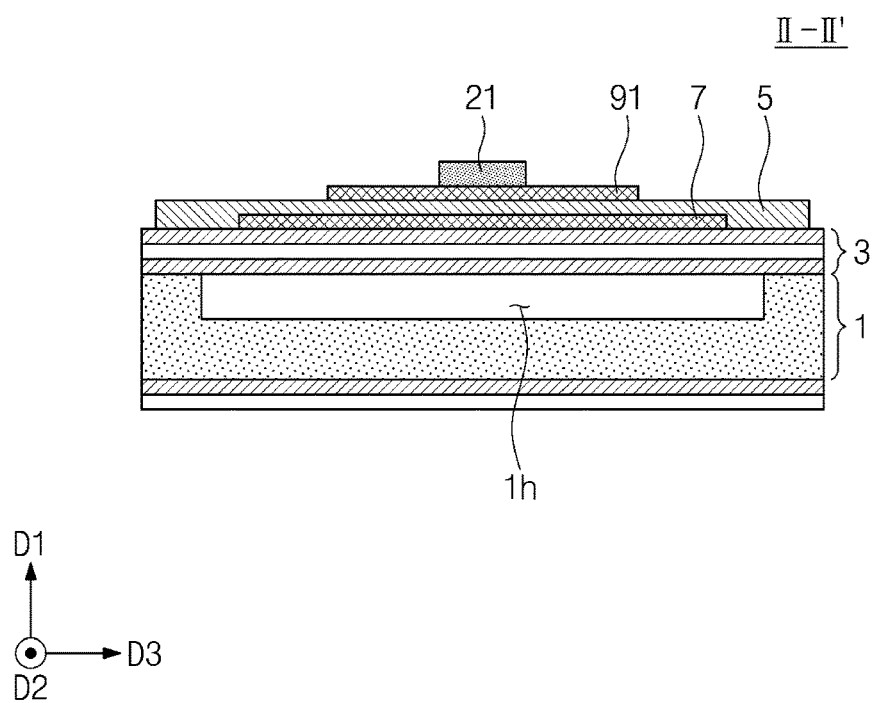
FIG. 10 is a cross-sectional view taken along line II-II' of FIG. 3.
Figure 11:
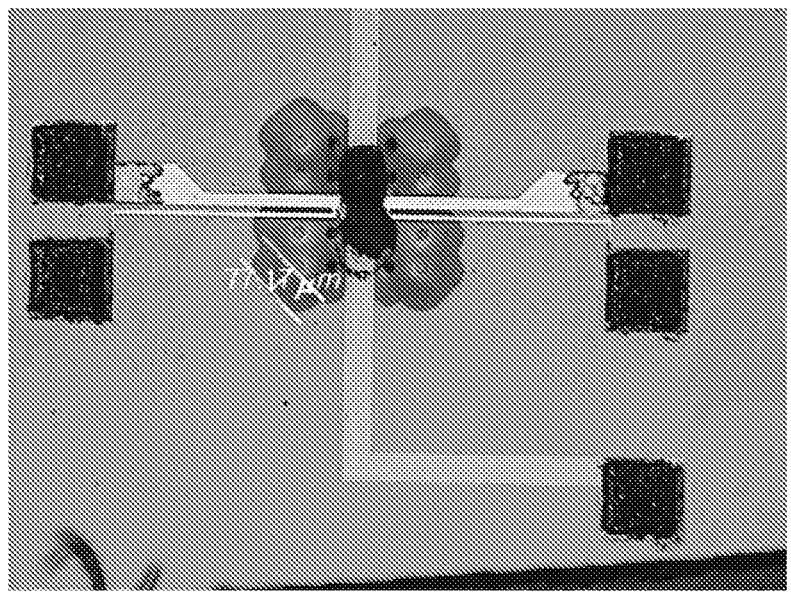
FIG. 11 is a plan photograph showing the gas sensor according to an embodiment of the inventive concept.

FIGS. 4 to 9 are cross-sectional views taken along line I-I' of FIG. 3 for sequentially explaining a method for manufacturing the gas sensor according to an embodiment of the inventive concept, FIG. 10 is a cross-sectional view taken along line II-II' of FIG. 3, and FIG. 11 is a plan photograph showing the gas sensor according to an embodiment of the inventive concept. Hereinafter, each of processes of the method for manufacturing the gas sensor will be described in detail.

The method for manufacturing the gas sensor may include: a process of laminating a first membrane on a substrate; a process of forming a heating structure on the first membrane; a process of laminating a second membrane on the first membrane and the heating structure; a process of forming a second membrane etching hole by patterning the second membrane; a process of forming a sensing electrode on the second membrane; a process of forming a first membrane etching hole in the first membrane through the second membrane etching hole; a process of etching a portion of the substrate through the first membrane etching hole and the second membrane etching hole; and a process of forming a sensing material structure on the sensing electrode.

Figure 4:
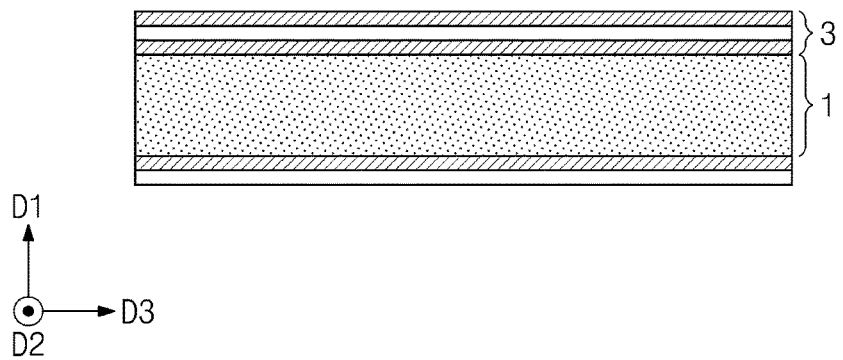
FIGS. 4 to 9 are cross-sectional views taken along line I-I' of FIG. 3 for sequentially explaining a method for manufacturing the gas sensor according to an embodiment of the inventive concept.

Referring to FIG. 4, the process of laminating the first membrane on the substrate may include a process of depositing a first membrane 3 on a substrate 1. The first membrane 3 may be formed by a method such as thermal oxidation deposition, sputtering deposition, and/or chemical vapor deposition (CVD). As described above, the first membrane 3 may have a structure having a plurality of layers of the silicon oxide (SiOx) and/or the silicon nitride (SiNx).

Figure 5:
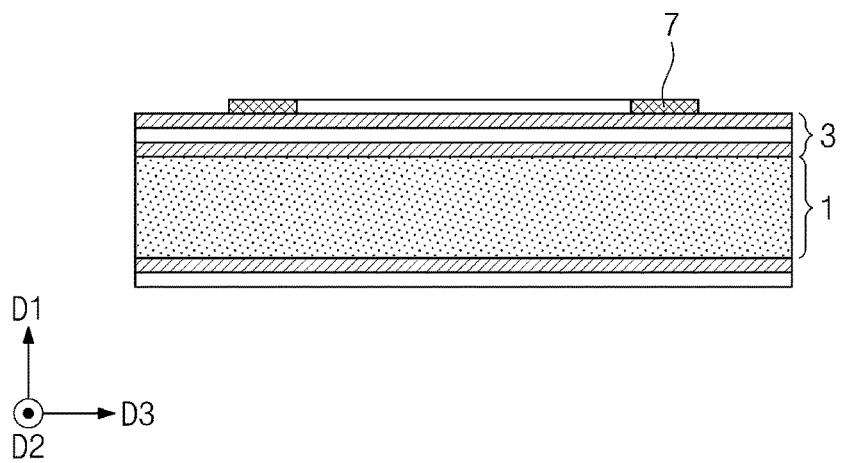
Figure 6:
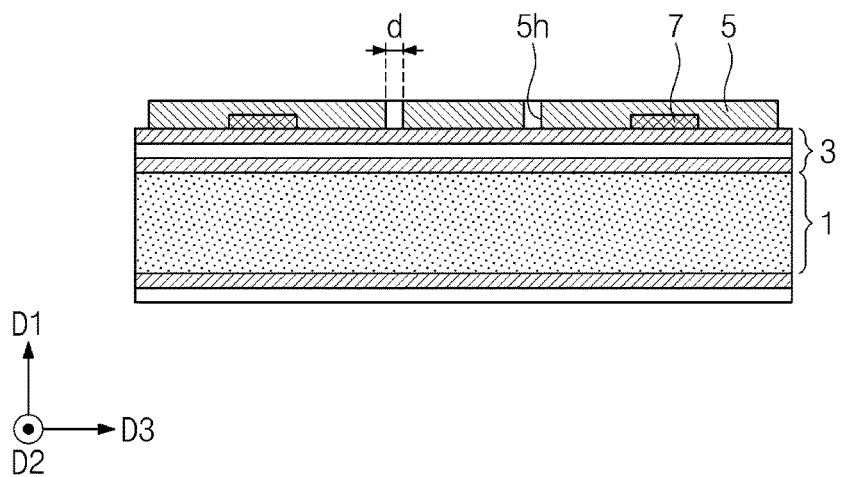

Referring to FIG. 5, the process of forming the heating structure on the first membrane may include a process of depositing a heating structure 7 on a top surface of the first membrane 3. For example, the heating structure 7 may be formed by sputtering deposition, e-beam deposition, and evaporation deposition. As illustrated in FIGS. 1 and 5, the heating structure 7 may be formed only on a partial area of the top surface of the first membrane 3.

Referring to FIG. 5, the process of laminating the second membrane on the first membrane and the heating structure may include a process of depositing a second membrane 5 on the first membrane 3 and the heating structure 7. The second membrane 5 may be formed by thermal oxidation deposition, sputtering deposition, and/or chemical vapor deposition (CVD).

The process of forming the second membrane etching hole by patterning the second membrane may include a process of forming a second membrane etching hole 5h by patterning a partial area of the second membrane 5 through a photolithography process and an etching process. The second membrane etching hole 5h may have a diameter d of about 3 μm to about 20 μm. More specifically, the second membrane etching hole 5h may have the diameter d of about 5 μm. In embodiments, the second membrane etching hole 5h may be horizontally spaced apart from the heating structure 7.

Figure 7:
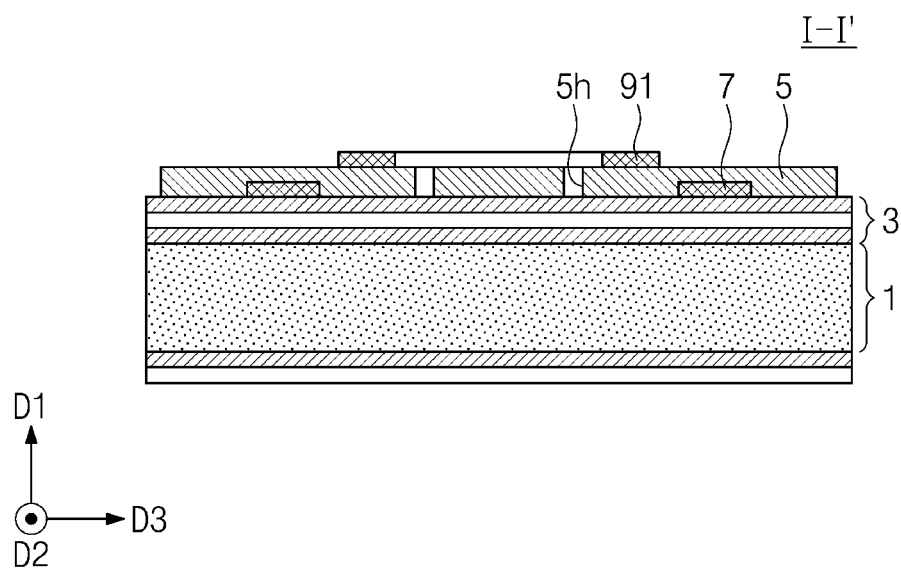

Referring to FIG. 7, the process of forming the sensing electrode on the second membrane may include a process of depositing a sensing electrode 91 on the second membrane 5. More specifically, the sensing electrode 91 may be formed by a method such as a sputtering deposition, e-beam deposition, and/or chemical vapor deposition (CVD). The sensing electrode 91 may be formed only on a partial area of a top surface of the second membrane 5. The sensing electrode 91 may be horizontally spaced apart the second membrane etching hole 5h.

Referring to FIG. 8, the process of forming the first membrane etching hole in the first membrane through the second membrane etching hole may include a process of forming a hole in a portion of the first membrane 3 through the second membrane etching hole 5h. The first membrane etching hole 3h may overlap the second membrane etching hole 5h on a plane. That is, the first membrane etching hole 3h may extend downward below the second membrane etching hole 5h. The first membrane etching hole 3h may have a diameter that is substantially equal or similar to the diameter d of the second membrane etching hole 5h.

Referring to FIGS. 9 and 10, the process of etching a portion of the substrate through the first membrane etching hole and the second membrane etching hole may include a process of forming an isolation space 1h by etching a portion of the substrate 1 through the first membrane etching hole 3h and the second membrane etching hole 5h. The etching process on the substrate 1 may include an isotropic etching process. More specifically, the etching process on the substrate 1 may be an isotropic etching process using xenon difluoride (XeF2). However, the embodiment of the present invention is not limited thereto. In the etching process on the substrate 1, a portion of the substrate may be remained to form a plurality of columns 13.

The process of forming the sensing material structure on the sensing electrode may include a process of forming a sensing material structure 21 on a partial area on the sensing electrode 91. The sensing material structure 21 may be formed through sol-gel, electrospinning, inkjet printing, screen printing, sputtering deposition, and/or chemical vapor deposition.

Referring to FIG. 11, it may be known that the etching hole is formed in the membrane. That is, the substrate may be etched through the etching hole formed in the membrane of FIG. 11.

The substrate may be etched by using only a few holes defined in the membranes by the gas sensor and the method for manufacturing the gas sensor according to the embodiments of the inventive concept. Thus, the membranes may not be damaged in the process of etching the substrate. Therefore, a manufacturing yield may improve, and a structural stability of the gas sensor may be secured. Also, as the diameter of the etching hole is restricted in a range from about 3 μm to about 20 μm, the membranes may not be damaged while the etching on the substrate is smoothly performed. Furthermore, since the etching holes are spaced apart from the heating structure and the sensing electrode on the plane, the substrate may be etched although a hole is not defined in the heating structure and the sensing electrode. Thus, since the hole is unnecessary to be defined in the heating structure and the sensing electrode, a structural stability of each of the heating structure and the sensing electrode may be secured.

The substrate may be spaced apart from the heating structure as the isolation space is defined in the substrate by the gas sensor and the method for manufacturing the gas sensor according to the embodiments of the inventive concept. Thus, the substrate may be thermally isolated from the heating structure. Therefore, electric power consumption may be reduced. Also, when the column is remained, the column may support the membrane or the like to secure a structural stability of the gas sensor.

The gas sensor and the manufacturing method thereof according to the embodiment of the inventive concept may reduce the electric power consumption and secure the structural stability.

The gas sensor and the manufacturing method thereof according to the embodiment of the inventive concept may prevent the damage of the membrane.

The gas sensor and the manufacturing method thereof according to the embodiment of the inventive concept may improve the manufacturing yield.

The object of the present invention is not limited to the aforesaid, but other objects not described herein will be clearly understood by those skilled in the art from descriptions below.

Although the embodiments of the present invention have been described, it is understood that the present invention should not be limited to these embodiments but various changes and modifications can be made by one ordinary skilled in the art within the spirit and scope of the present invention as hereinafter claimed. Thus, the above-disclosed embodiments are to be considered illustrative and not restrictive.

What is claimed is:

1. A gas sensor comprising:
   a substrate;
   a first membrane disposed on the substrate;
   a heating structure disposed on the first membrane;
   a second membrane disposed on the heating structure;
   a sensing electrode disposed on the second membrane; and
   a sensing material structure disposed on the sensing electrode,
   wherein the substrate provides an isolation space defined by a recessed surface obtained as a portion of a top surface of the substrate is spaced downward from a bottom surface of the first membrane,
   the first membrane provides a first membrane etching hole that vertically extends to connect a top surface and the bottom surface of the first membrane and is connected with the isolation space,
   wherein the first membrane etching hole has a diameter of about 3 μm to about 20 μm,
   wherein the substrate further comprises an inner sidewall connecting the recessed surface and another portion of the top surface of the substrate,
   wherein the substrate further comprises a plurality of columns penetrating the isolation space,
   each of the plurality of columns vertically extends to connect the bottom surface of the first membrane with the recessed surface, and
   each of the plurality of columns is spaced apart from the inner sidewall of the substrate.

2. The gas sensor of claim 1, wherein the heating structure is not in overlap with the first membrane etching hole in terms of a plane.

3. The gas sensor of claim 1, further comprising:
   a compensation electrode disposed on the second membrane; and
   a compensation material structure disposed on the compensation electrode.

4. The gas sensor of claim 1, wherein four first membrane etching holes are provided.

5. The gas sensor of claim 1, wherein the first membrane etching hole has a diameter of about 5 μm.

6. The gas sensor of claim 1, wherein the second membrane provides a second membrane etching hole that vertically extends to connect a top surface and a bottom surface of the second membrane and is connected with the first membrane etching hole.

7. The gas sensor of claim 1, wherein the substrate comprises silicon (Si), aluminum oxide ($Al_2O_3$), magnesium oxide (MgO), quartz, gallium-nitrogen (GaN), gallium-arsenic (GaAs), polycarbonate (PC), polyethylene terephthalate (PET), polyethersulfone (PES), polyethylene naphthalate (PEN) or polyimide (PI), and
   each of the first membrane and the second membrane comprises silicon oxide ($SiOx$) or silicon nitride ($SiNx$).

8. A method for manufacturing a gas sensor, comprising:
   laminating a first membrane on a substrate;
   forming a heating structure on the first membrane;
   laminating a second membrane on the first membrane and the heating structure;

forming a second membrane etching hole by patterning the second membrane;

forming a sensing electrode on the second membrane;

forming a first membrane etching hole in the first membrane through the second membrane etching hole; and etching a portion of the substrate through the first membrane etching hole and the second membrane etching hole, wherein the forming of a portion of the substrate comprises forming an isolation space by allowing a portion of a top surface of the substrate to be recessed downward, the first membrane etching hole has a diameter of about 3 µm to about 20 µm, wherein the substrate further comprises an inner sidewall connecting the recessed surface and another portion of the top surface of the substrate, wherein the substrate further comprises a plurality of columns penetrating the isolation space, each of the plurality of columns vertically extends to connect the bottom surface of the first membrane with the recessed surface, and each of the plurality of columns is spaced apart from the inner sidewall of the substrate.

9. The method of claim 8, wherein the heating structure is not in overlap with the first membrane etching hole in terms of a plane.

10. The method of claim 8, wherein the etching of a portion of the substrate comprises allowing a plurality of columns surrounded by the isolation space to be remained, and each of the plurality of columns vertically extends to connect a bottom surface of the first membrane with a recessed surface.

11. The method of claim 8, wherein each of the laminating of the first membrane on the substrate and the laminating of the second membrane on the first membrane and the heating structure is performed by using thermal oxidation deposition, sputtering deposition, or chemical vapor deposition.

12. The method of claim 8, wherein four first membrane etching holes are provided.

* * * * *